United States Patent [19]

Maeda

[11] 4,329,874
[45] May 18, 1982

[54] CALORIMETRIC APPARATUS

[75] Inventor: Shosaku Maeda, Atsugi, Japan

[73] Assignee: Honeywell Inc., Minneapolis, Minn.

[21] Appl. No.: 208,136

[22] Filed: Nov. 19, 1980

[30] Foreign Application Priority Data

Jul. 4, 1980 [JP] Japan .................................. 55-45857

[51] Int. Cl.$^3$ ...................... G01K 17/00; G01N 25/30
[52] U.S. Cl. .................................. 73/190 CV; 422/51; 422/95
[58] Field of Search .............. 73/190 CV; 422/51, 95, 422/97

[56] References Cited
U.S. PATENT DOCUMENTS 2,197,370  4/1940  Sullivan .................................. 73/190
3,777,562  12/1973  Clingman, Jr. ......................... 73/190

*Primary Examiner*—Herbert Goldstein
*Attorney, Agent, or Firm*—Laurence J. Marhoefer; Lockwood D. Burton; Mitchell J. Halista

[57] ABSTRACT

A calorimetric apparatus for determining the calorific content of a fuel gas uses a reactor for producing oxidation of the fuel gas and a combustion gas in the presence of a catalytic oxidizer. The catalytic oxidizer is mounted on one end of a thermo-electric element which element has a heat absorbing end and a heat emitting end when energized by an electric current to produce a Peltier effect. The catalytic end of the element is mounted within the reactor while the other end is located outside of the reactor. The temperatures of the ends of the element are detected by a controller and the difference therebetween is maintained at a predetermined level during the catalytic reaction by the controller developing a control signal to control the supply of the electric current to the element. A display control signal is derived from the control signal by the controller and used to control a display for indicating the calorific content of the fuel gas.

10 Claims, 3 Drawing Figures

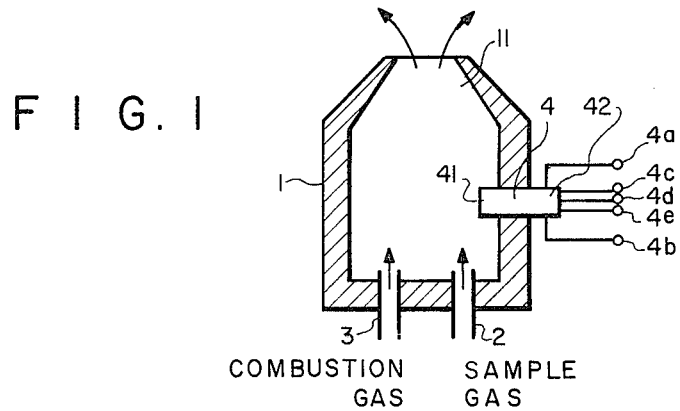
F I G. 1
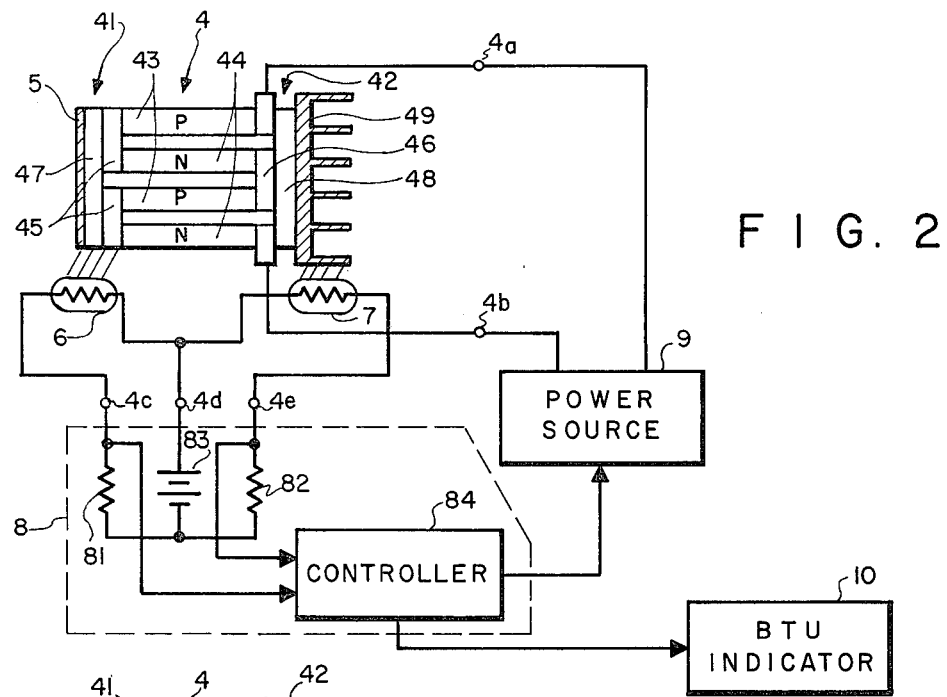
F I G. 2
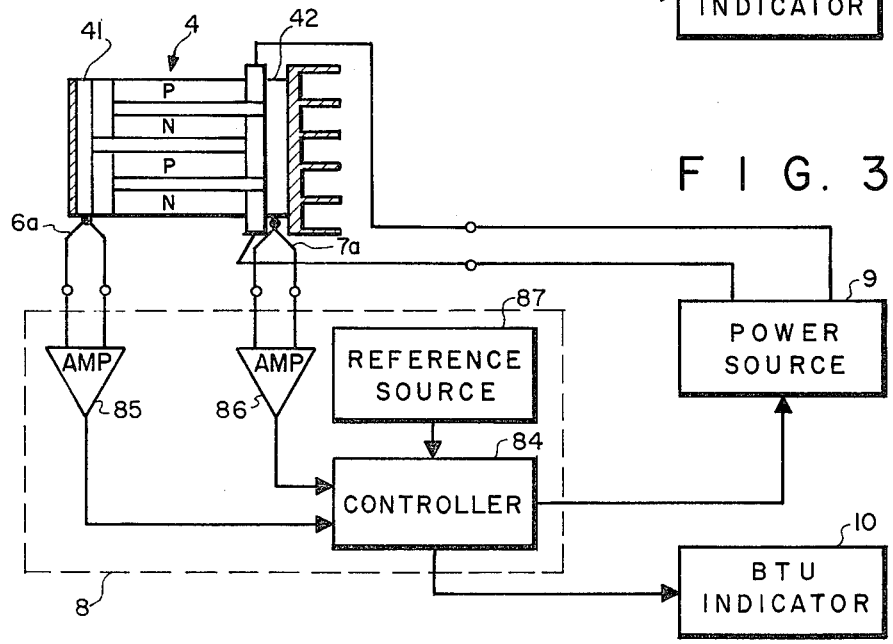
F I G. 3

CALORIMETRIC APPARATUS

BACKGROUND OF THE INVENTION

1. Field of the Invention

This invention relates to a calorimetric apparatus which is particularly suitable for determining the calorific value of fuel gas.

2. Description of the Prior Art

There is an apparatus known as a calorimeter which burns a predetermined quantity of gas to heat water, etc., measures the temperature of the water, etc., and compares it with the original temperature thereof, whereby the calorific value of the gas is determined. That apparatus is, however, unable to determine an accurate calorific value, since it has difficulty in completely collecting the heat generated by combustion of the gas and without allowing a part of it to escape. It is also difficult to establish predetermined conditions in the combustion chamber if that apparatus is small. That apparatus does not lend itself to quick determination, since it requires a considerable time before it becomes ready to work for the purpose intended after it is placed in operation. Another disadvantage of that apparatus lies in the formation of a flame which is not desirable from the standpoint of safety or operation.

Another calorimetric method known in the art employs a gas chromatograph by which the quantities of the combustible ingredients of a sample gas are analyzed, so that the total calorific value of the gas may be obtained by calculation. The use of such an apparatus is, however, very expensive.

SUMMARY OF THE INVENTION

In view of the aforementioned disadvantages of the prior art, it is an object of this invention to provide a small and inexpensive calorimetric apparatus which requires only a minor quantity of a sample gas to determine its calorific value quickly and accurately without burning it, in accordance with a principle which is entirely different from those on which the prior art has been based.

According to this invention, this object is attained by providing a thermo-electric element having a heat absorbing portion and a heat emitting portion, and mounted so that one of those portions may be disposed inside a reactor into which sample and combustion gases are introduced, while the other portion is disposed outside the reactor, detecting a difference in temperature between those portions, transmitting a feedback control signal responsive to such temperature difference to a power supply unit to control the supply of an electric current to the thermo-electric element to thereby maintain the aforementioned temperature difference constant, and further transmitting a display signal corresponding to the feedback control signal to display the calorific value of the sample gas.

BRIEF DESCRIPTION OF THE DRAWINGS

A better understanding of the present invention may be had when the following detailed description is read in connection with the accompanying drawings, in which:

FIG. 1 is a schematic vertical sectional view of the calorimetric apparatus embodying an example of the present invention, FIG. 2 is a circuit diagram suitable for use with the apparatus shown in FIG. 1, and FIG. 3 is a modified arrangement of the circuit diagram shown in FIG. 2.

DESCRIPTION OF THE PREFERRED EMBODIMENT

Referring to FIG. 1, the apparatus comprises a bottle-shaped reactor 1 having a capacity of about 50 to 100 cc, and provided at its top with an opening 11 which defines a discharge passage. A pair of gas lines 2 and 3 extend into the reactor 1 through the bottom thereof, and define a passage for introducing a sample gas thereinto, and a passage for introducing combustion gas suitable for reacting with the sample gas there into, respectively. The reactor 1 has a side wall provided with a thermoelectric element hereinafter referred to as a thermoelement 4 which bases its functions on the Peltier effect such thermo-electric elements being well-known in the art. The thermoelement 4 includes a portion 41 for absorbing heat, and another portion 42 for emitting heat, when an electric current flow is supplied thereto. The heat absorbing portion 41 is disposed inwardly of the side wall of the reactor 1, while the heat emitting portion 42 is disposed outwardly thereof. Electric current is supplied to the thermoelement 4 through electrical conductors and terminals 4a and 4b thereof. Concurrently, the temperatures of the heat absorbing portion 41 and the heat emitting portion 42 are sensed through electrical conductors and terminals 4c, 4d and 4e.

Sample fuel gas and combustion gas, such as oxygen and air, are blown into the reactor 1 continuously as a constant flow rate through the gas lines 2 and 3, respectively, to produce a homogeneous gaseous mixture filling the reactor 1. This gaseous mixture is gradually discharged through the discharge opening 11, and the atmosphere in the reactor 1 is replaced progressively by a fresh gaseous mixture. If it is necessary to maintain the concentration of the sample gas in the reactor at its lower explosion limit, it is appropriate to supply the combustion gas at a rate of about 200 cc/min. for 1 cc/min. of the sample gas, whereby an atmosphere having an excess content of combustion gas is maintained in the reactor 1. When the reactor 1 has thus been filled with the gaseous mixture, the apparatus shown in FIG. 1 produces an oxidation of sample gas which process heats the heat absorbing portion 41 as will hereinafter be described in further detail.

As shown in FIG. 2, the thermoelement 4 comprises an alternately end coupled assembly of two kinds of metals 43 and 44 having largely different degrees of thermoelectric power. When an electric current flow is supplied to the metals 43 and 44, heat is absorbed by end junctions 45, and emitted by end junctions 46, by virtue of the Peltier effect. The end junctions 45 absorbing heat are combined to form the heat absorbing portion 41, while the junctions 46 emitting heat define the heat emitting portion 42. A ceramic insulator 47 is secured to the end junctions 45, and has a surface covered with an oxidation catalyzing substance 5 consisting mainly of a highly active metal, e.g., platinum. Likewise, a ceramic insulator 48 is secured to the end junctions 46, and a heat releasing member 49, e.g., metal fins, is attached to the outer surface of the insulator 48. Thus, the oxidation catalyzing substance 5 is brought into contact with the gas mixture in the reactor 1, while the heat releasing member 49 is exposed to the open atmosphere outside of the reactor 1.

A temperature sensor element or thermistor 6 is provided on, i.e., thermally associated with, the heat absorbing portion 41 to detect its temperature, and, similarly, a thermistor 7 is provided on the heat emitting portion 42. The respective temperatures detected by the thermistors 6 and 7 affect operational characteristics of corresponding ones of the thermistors 6 and 7 to enable the thermistors 6 and 7 to provide input signals to a control system 8. The control system 8, in turn, produces an output signal representing the difference between those temperatures. The control system 8 comprises a pair of resistances 81 and 82 defining a bridge circuit in combination with the thermistors 6 and 7, respectively, a power source 83 supplying an electric current to the bridge circuits and a controller unit 84 adapted to receive unbalanced outputs from the bridge circuits and to transmit a control signal representing the temperature difference between the inner and outer portions 41 and 42 of the thermoelement 4. This control signal is applied to a power source unit 9 which is used to supply an electric current to the thermoelement 4. The controller unit 84 also transmits a display control signal derived from the aforesaid temperature difference to a calorimetric or BTU display unit 10.

In operation, the sample gas undergoes oxidation with the combustion gas and generates heat when it is brought into contact with the oxidation catalyzing substance 5. This heat is absorbed by the heat absorbing portion 41, and does not raise the temperature of the atmosphere in the reactor 1. Such a greater temperature difference between the two portions 41 and 42 of the thermoelement 4 results in a greater difference between the resistances of the thermistors 6 and 7. Such an unbalance between the thermistors 6 and 7 causes a change in the bridge output which is applied to the controller unit 84, so that the controller unit 84, in turn, transmits a control signal to the power source unit 9. This control signal is used to provide an appropriate control for the output of the power source unit 9 to maintain the temperature difference between the two portions 41 and 42 substantially at a predetermined level which prevailed before the heating effect produced by the oxidation of the sample gas reaction. This control effect is based on the fact that the heat absorbing and emitting operation of the thermoelement 4 is directly related to the amount of the electric current applied thereto. Accordingly, by varying the electric current through the thermoelement 4, the effect of the added heating produced by the catalytic oxidation of the sample gas can be offset to restore the resistances of the thermistors 6 and 7 to their prior value which would restore the prior state or balance of the bridge circuit. The controller unit 84, thus, acts to control the output of the power source 9 until the bridge circuit is rebalanced by the change in the heating and cooling effect of the thermoelement 4. Thus, the change in the temperature difference between the two portions 41 and 42 is solely due to the heat produced by oxidation of the sample gas, and the feedback control signal transmitted by the control unit 84 to the power supply 9 precisely represents such a temperature difference, so that it can be converted by the controller 8 into a display control signal indicating such temperature difference. This display control signal is applied to the display unit 10 to produce a display of the quantity of the heat produced by the oxidation of the sample gas on the display unit 10. As oxidation is a reaction which is chemically equivalent to combustion, such a display on the display unit 10 indicates the calorific value of the sample gas.

According to the apparatus as hereinabove described, it is possible, without the sacrifice of reliability in operation, to use a reactor of the type in which its inside temperature is easily affected by the temperature of the atmosphere surrounding it, since the temperature difference between the heat absorbing and emitting portions of the thermoelement is maintained constant, whether before or after the reaction. Moreover, if the temperature of the outer portion of the thermoelement is taken as a reference, its heat absorbing portion disposed in the reactor is maintained at a constant temperature. It is, therefore, possible to maintain constant the efficiency or activity of the catalyst on the thermoelement, and the thermal conditions involved, including heat loss, which might otherwise be affected by variation in the catalyst temperature. Thus, the aforesaid apparatus would also exhibit a high degree of accuracy in operation with a high degree of reproducibility.

Attention is now directed to FIG. 3 which shows a modified form of the control system 8 shown in FIG. 2. The modified control system 8A comprises a pair of thermocouples 6a and 7a detecting the temperatures of the heat absorbing and emitting portions 41 and 42, respectively, of the thermoelement 4, a pair of amplifiers 85 and 86 adapted to amplify the output signals from the thermocouples 6a and 7a, respectively, and a reference signal source 87. The outputs of the amplifiers 85 and 86 correspond to the temperatures of the heat absorbing and emitting portions 41 and 42, respectively, as represented by the corresponding thermocouple signal. The outputs from the amplifers 85 and 86 are received into the controller unit 84 which, in turn, compares them with the reference signal from the reference signal source 87. The controller unit 84 produces a control signal corresponding to the temperature difference between the two portions 41 and 42. The control signal from the controller 84 is applied to the power source 9 and the further operation of the apparatus shown in FIG. 3 is the same as its counterpart shown in FIG. 2.

Various other arrangements are obviously available for detecting such temperature differences. Moreover, it is possible to reverse the position of the thermoelement relative to the reactor, so that the oxidation catalyst may be positioned on the heat emitting portion of the thermoelement disposed within the reactor to increase the efficiency or activity of the catalyst.

While the reactor employed in the aforementioned embodiments has been described as being in the form of a bottle having a capacity of 50 to 100 cc, it is equally possible to use a larger or smaller reactor having a variety of different shapes to provide a homogeneous mixture of the gases therein. It is also possible to provide the reactor with a cover to prevent any gaseous mixture from leaving the reactor and to thereby permit the gas mixture to be agitated more effectively. It is further possible for the apparatus to include a device for mixing predetermined proportions of sample and combustion gases and to introduce a mixture thereof into the reactor through a single passage, instead of providing separate passages for those gases as hereinbefore described. Additionally, the oxidation catalyst to be applied to the thermoelement does not always need to consist of platinum, but may also be composed of any other metal belonging to Groups I, V, VI and VIII of the Periodic Table, such as copper, silver, vanadium, chromium, iron, cobalt, nickel and palladium, alone or in combination with any other active ingredient.

It is obvious from the foregoing description that the calorimetric apparatus of this invention provides advantages which have not hitherto been realizable by the prior art. It is simple and compact in construction, and inexpensive to manufacture. It requires only a minor quantity of sample gas, and the use of the heat produced by its oxidation ensures very quick and accurate determination of its calorific value, since the escape of such heat is minimized. The apparatus of the present invention can continuously perform accurate determination of the calorific value of any particular gas, even if the gas may change with the lapse of time. Moreover, the absence of any flame drastically improves the safety and reliability of the operation of the present invention.

The embodiments of the invention in which an exclusive property or privilege is claimed are defined as follows:

1. A calorimetric apparatus comprising:
   a reactor having a passage means for introducing sample and combustion gases thereinto,
   a thermoelement having a first portion disposed inside said reactor and a second portion disposed outside said reactor, one of said first and second portions being adapted to absorb heat, while the other of said portions is adapted to emit heat, when said thermoelement is supplied with an electric current,
   an oxidation catalyzing element provided on said first portion of said thermoelement,
   a first temperature sensor element provided on said first portion of said thermoelement,
   a second temperature sensor element provided on said second portion of said thermoelement,
   a power source unit for supplying the electric current to said thermoelement,
   a control system means connected to said first and second sensor element and said power source unit for producing an output control signal representative to a difference in temperature between said first and second portions for controlling the electric current supplied by said power source unit, and
   display means connected to said control system and responsive to a display control signal corresponding to said output signal, whereby the calorific value of said sample gas is displayed on said display means.

2. A calorimetric apparatus as set forth in claim 1 wherein said catalyzing element includes a platinum coating.

3. A calorimetric apparatus as set forth in claim 1 where said catalyzing element includes a coating of a metal from Groups I, V, VI, and VIII of the Periodic Table.

4. A calorimetric apparatus as set forth in claim 1 wherein said first and second sensor elements are thermistors.

5. A calorimetric apparatus as set forth in claim 1 wherein said first and second sensor elements are thermocouples.

6. A calorimetric apparatus as set forth in claim 1 wherein said reactor includes a second passage means for discharging said gases therefrom.

7. A calorimetric apparatus as set forth in claim 1 wherein said first portion of said thermoelement is arranged to absorb heat.

8. A calorimetric apparatus as set forth in claim 1 wherein said first portion of said thermoelement is arranged to emit heat.

9. A calorimetric apparatus as set forth in claim 1 wherein said first and second sensors are thermistors and are arranged in adjacent legs of a bridge circuit supplied with a direct current with the output of said bridge circuit being applied to the input of said control system means.

10. A calorimetric apparatus as set forth in claim 1 wherein said first and second sensors are thermocouples and wherein said control system means includes a reference signal source and a controller means arranged to compare the difference in output signals between said first and second sensors and an output signal from said reference signal source to produce said output control signal.

* * * * *